United States Patent
Lee et al.

(10) Patent No.: US 12,048,689 B2
(45) Date of Patent: Jul. 30, 2024

(54) PHARMACEUTICAL COMPOSITION FOR PREVENTING OR TREATING INFLAMMATORY BOWEL DISEASE ACTING AS A FUNCTIONAL ANTAGONIST FOR S1PR1 AND S1PR4

(71) Applicant: NEXTGEN BIOSCIENCE CO., LTD., Seongnam-si (KR)

(72) Inventors: Bong Yong Lee, Seoul (KR); Yang Hae Park, Seoul (KR); Eun Jeong Kim, Seongnam-si (KR)

(73) Assignee: NEXTGEN BIOSCIENCE CO., LTD., Seongnam-si (KR)

( * ) Notice: Subject to any disclaimer, the term of this patent is extended or adjusted under 35 U.S.C. 154(b) by 0 days.

(21) Appl. No.: 18/477,175

(22) Filed: Sep. 28, 2023

(65) Prior Publication Data
US 2024/0041836 A1 Feb. 8, 2024

Related U.S. Application Data (63) Continuation of application No. PCT/KR2022/007785, filed on May 31, 2022.

(30) Foreign Application Priority Data

Mar. 23, 2022 (KR) .................. 10-2022-0036306

(51) Int. Cl.
A61K 31/4192 (2006.01)
A61K 45/06 (2006.01)
A61P 1/04 (2006.01)

(52) U.S. Cl.
CPC .......... A61K 31/4192 (2013.01); A61K 45/06 (2013.01); A61P 1/04 (2018.01)

(58) Field of Classification Search
CPC .............................. A61K 31/4192; A61P 1/04
See application file for complete search history.

(56) References Cited

U.S. PATENT DOCUMENTS

2023/0339869 A1* 10/2023 Bae .................. A61P 21/00

FOREIGN PATENT DOCUMENTS

| AU | 2019264073 A1 | 11/2020 |
| AU | 2021202271 A1 | 5/2021 |
| KR | 10-2017-0087813 A | 7/2017 |
| KR | 10-2018-0036318 A | 4/2018 |
| KR | 10-2018-0110499 A | 10/2018 |

OTHER PUBLICATIONS

Camilleri et al., "Efficacy and safety of alosetron in women with irritable bowel syndrome: a randomized, placebo-controlled trial", Lancet, vol. 355, No. 9209, pp. 1035-1040 (2000).*
Laurent Peyrin-Biroulet et al., "Modulation of sphingosine-1-phosphate in inflammatory bowel disease", Autoimmunity Reviews, 2017, pp. 495-503, vol. 16, Issue 5.
Roberta Izzo et al., "Sphingosinc-1-phosphate receptor: a novel therapeutic target in ulcerative colitis", Expert Review of Clinical Immunology, Published online Aug. 8, 2016, 4 pages.
Tobias Schulze et al., "Sphingosine-1-phospate receptor 4 (S1P4) deficiency profoundly affects dendritic cell function and TH17-cell differentiation in a murine model", The FASEB Journal • Research Communication, Nov. 2011, pp. 4024-4036, vol. 25.
International Search Report for PCT/KR2022/007785, dated Aug. 4, 2022.
Written Opinion for PCT/KR2022/007785, dated Aug. 4, 2022.
Communication dated Dec. 15, 2023 issued by the Canadian Patent Office in application No. 3212009.
M. Argollo, et al., "Modulation of sphingosine-1-phosphate in ulcerative colitis", Expert Opinion on Biological Therapy, vol. 20, No. 4, 2020, pp. 413-420 (9 pages total).

* cited by examiner

*Primary Examiner* — Kevin E Weddington
(74) *Attorney, Agent, or Firm* — Sughrue Mion, PLLC (57) ABSTRACT

The present invention relates to a pharmaceutical composition for preventing or treating inflammatory bowel disease acting as a functional antagonist for S1PR1 and S1PR4 of S1P receptors, and more specifically, to a pharmaceutical composition including, as an active ingredient, a sphingolipid compound which does not cause cardiovascular side effects by acting as a functional antagonist for S1PR1 and S1PR4 and has an effect of preventing or treating inflammatory bowel disease.

6 Claims, 5 Drawing Sheets

Disease activity index (DAI) of DSS-induced colitis mice.
The mice were grouped with Normal, 2.5% DSS + Vehicle,
2.5% DSS + MTX (3 mg/kg; IP; TIW), 2.5% DSS + Ozanimod (5 mg/kg; PO; QD),
2.5% DSS + NXC736 (5 mg/kg; PO; QD), 2.5% DSS + NXC736 (10 mg/kg; PO; QD),
Data are expressed as the mean ± SEM.
* = $p < 0.05$,  = $p < 0.01$, and * = $p < 0.001$ versus Vehicle control Area under the curve (AUC) of disease activity index in
DSS-induced colitis mice. The mice were grouped with Normal,
2.5% DSS + Vehicle, 2.5% DSS + MTX (3 mg/kg; IP; TIW),
2.5% DSS + Ozanimod (5 mg/kg; PO; QD), 2.5% DSS + NXC736 (5 mg/kg; PO; QD),
2.5% DSS + NXC736 (10 mg/kg; PO; QD), Data are expressed as
the mean ± SEM. * = $p < 0.05$,  = $p < 0.01$, and * = $p < 0.001$ versus Vehicle control.

FIG. 3

| Group / Concentration (μM) | | $I_{pre}$ (pA) | $I_{post}$ (pA) | $I_{rel}$ | Suppression rate (%) | Compensated suppression rate (%) | $IC_{50}$ (μM) | H |
|---|---|---|---|---|---|---|---|---|
| A | Mean | 1279 | 1238 | 0.9682 | 3.18 | 0.00 | 12.94 | 1.527 |
| 0 | S.D. | 50 | 37 | 0.0399 | 3.99 | 4.12 | | |
| | N | 3 | 3 | 3 | 3 | 3 | | |
| B | Mean | 894 | 783 | 0.8720 | 12.80 | 9.94 | | |
| 1 | S.D. | 254 | 234 | 0.0190 | 1.90 | 1.96 | | |
| | N | 3 | 3 | 3 | 3 | 3 | | |
| C | Mean | 1147 | 953 | 0.8328 | 16.72 | 13.98 | | |
| 3 | S.D. | 371 | 295 | 0.0434 | 4.34 | 4.48 | | |
| | N | 3 | 3 | 3 | 3 | 3 | | |
| D | Mean | 1250 | 803 | 0.6291 | 37.09 | 35.03 | | |
| 10 | S.D. | 1085 | 722 | 0.1170 | 11.70 | 12.09 | | |
| | N | 3 | 3 | 3 | 3 | 3** | | |
| E | Mean | 968 | 170 | 0.1683 | 83.17 | 82.62 | | |
| 30 | S.D. | 289 | 107 | 0.0707 | 7.07 | 7.31 | | |
| | N | 3 | 3 | 3 | 3 | 3** | | |
| F | Mean | 1427 | 101 | 0.0712 | 92.88 | 92.64 | | |
| 0.1 | S.D. | 608 | 48 | 0.0160 | 1.60 | 1.66 | | |
| | N | 5 | 5 | 5 | 5 | 5*** | | |

A: Negative control group (External bath solution), B-E: Test substance group (NXC736), F: Positive control group (E-4031)
$I_{pre}$: Pre-treatment current
$I_{post}$: Treatment current
$I_{rel}$: Relative current
S.D.: Standard deviation
N: Number of cells
$IC_{50}$: The half-maximal inhibitory concentration
H: Hill coefficient
**$p<0.01$ : Significantly different from the negative control group (A) by Dunnett's t-test.
***$p<0.01$: Significantly different from the negative control group (A) by Student's t-test.

PHARMACEUTICAL COMPOSITION FOR PREVENTING OR TREATING INFLAMMATORY BOWEL DISEASE ACTING AS A FUNCTIONAL ANTAGONIST FOR S1PR1 AND S1PR4

CROSS REFERENCE TO RELATED APPLICATIONS

This application is a Rule 53(b) Continuation of International Application No. PCT/KR2022/007785 filed on May 31, 2022, claiming priority based on Korean Patent Application No. 10-2022-0036306 filed on Mar. 23, 2022, the respective disclosures of all of the above of which are incorporated herein by reference in their entirety.

TECHNICAL FIELD

The present invention relates to a pharmaceutical composition for preventing or treating inflammatory bowel disease acting as a functional antagonist for S1PR1 and S1PR4, and more specifically, the present invention relates to a pharmaceutical composition including a sphingolipid compound which does not cause cardiovascular side effects by acting as a functional antagonist for S1PR1 and S1PR4 and has an effect of preventing or treating inflammatory bowel disease.

BACKGROUND ART

Inflammatory bowel disease (IBD) is a disease that causes chronic inflammation and ulcers in the intestine, and along with genetic factors, an excessive immune response of our body to bacteria that are normally present in the intestine is considered to be an important pathogenic factor. Ulcerative colitis (UC) and Crohn's disease (CD) are typical inflammatory bowel diseases.

Crohn's disease refers to a chronic inflammatory bowel disease that may occur anywhere in the gastrointestinal tract, from the mouth to the anus. In Crohn's disease, inflammation invades all layers of the intestines, and a pattern, in which pathological changes are distributed, is not continuous and sporadically appears in many cases, unlike ulcerative colitis. In particular, the disease most often occurs in the ileocecal area that is a site where the large intestine is connected with the small intestine, followed by the large intestine, the distal end part of the ileum, the small intestine, and the like. Although the exact cause of Crohn's disease is not yet known, it is considered to be caused by an excessive immune response of our body to bacteria that are normally present in the intestine, along with environmental and genetic factors.

Ulcerative colitis, which causes inflammation or ulceration of the large intestine mucosa, is manifested in the form of multiple ulcers by causing bleeding while the large intestine mucosa becomes congested and swollen, and is divided into three types: chronic recurrent, chronic persistent, and acute fulminant colitis. Typically, ulcerative colitis is most often a chronic recurrent disease, and in this case, the symptoms worsen as the disease recurs, and in chronic persistent colitis, severe symptoms persist for about 6 months. In the case of acute fulminant colitis, the symptoms are very severe and accompanied by high fever, and there is a risk of death within a few weeks after the onset of symptoms. Although the cause of ulcerative colitis has not been elucidated to date, it is known that the cause is related to environmental factors such as irregular eating habits and external stress or genetic factors such as family history, immunological abnormalities in the large intestine wall, abnormal immune responses of our body to normal bacteria distributed in the intestines, and the like. Typically, ulcerative colitis was a disease with a high incidence in Europe and North America, where meat is mainly eaten, but recently, the incidence has tended to increase in the East Asia region including South Korea due to westernized eating habits. As a method for treating ulcerative colitis, surgical treatment is aimed at complete cure, and removes all affected large intestine sites. Meanwhile, as a drug treatment method, anti-inflammatory agents such as sulfasalazine and mesalamine, corticosteroids such as hydrocortisone, dexa, PD and Medron, immunosuppressants such as azathioprine and purinethol, and antibiotics such as metronidazole, and biological agents such Remicade are used, but there has been no drug treatment method capable of completely curing ulcerative colitis to date. Most commonly, therapeutic agents such as anti-inflammatory agents such as sulfasalazine and mesalamine and corticosteroids are used, and drugs such as immunosuppressants and antibiotics are appropriately selected and used depending on the patient's conditions. Among them, sulfasalazine has been used as a standard treatment method for ulcerative colitis for decades, but high doses and long-term use induce oxidative stress and may cause side effects such as nausea, heartburn, headaches, dizziness, anemia, and skin rashes, and in rare cases, these drugs may induce hepatitis, pancreatitis, pneumonia, and the like. Moreover, although ulcerative colitis in which pathological changes appear only in the rectum can be completely cured by only temporary drug treatment, ulcerative colitis in which pathological changes occur in areas above the rectum have a high recurrence frequency and may progress to complications such as intestinal perforation and toxic megacolon, and colorectal cancer.

Thus, there is a continuous need for the development of a drug that is capable of being used for the treatment of inflammatory bowel disease and has excellent drug efficacy, and is safe in terms of side effects and toxicity.

Thus, while conducting intensive studies to develop an independent compound that selectively acts on S1P subtype receptors among sphingolipid compounds, the present inventors confirmed that the compound according to the present invention does not cause cardiovascular side effects due to non-selectivity with respect to S1PR subtypes and simultaneously has an effect of preventing or treating inflammatory bowel disease by specifically binding to S1PR1 and S1PR4 receptors to serve as a functional antagonist, thereby completing the present invention.

RELATED ART DOCUMENT

Patent Document

Korean Patent Application Laid-Open No. 10-2017-0087813 (Jul. 31, 2017)

DISCLOSURE

Technical Problem

The present invention provides a pharmaceutical composition including, as an active ingredient, a compound which does not cause cardiovascular side effects and has a pharmacological activity of preventing or treating inflammatory bowel disease.

Technical Solution

The pharmaceutical composition for preventing or treating inflammatory bowel disease according to the present invention includes, as an active ingredient, a material selected from a compound represented by the following Chemical Formula 1, an optical isomer thereof or a pharmaceutically acceptable salt thereof.

[Chemical Formula 1]

Here,
R$^1$ is hydrogen;
R$^2$ is hydrogen or an acetyl group;
X is a single bond, a C$_2$ alkylene, or a C$_2$ alkenylene;
A is a 5-membered heteroarylene including three N atoms;
B is a C$_{2-11}$ straight or branched alkylene;
C is a single bond or phenylene; and
D is selected from the group consisting of hydrogen, phenyl and a C$_{1-6}$ alkyl.
R$^2$ can be hydrogen.
X can be a C$_2$ alkylene.
B can be a straight C$_{2-11}$ alkylene.

The compound represented by Chemical Formula 1 can be any one compound selected from the following compound group.

(1) 2-amino-2-(2-(1-decyl-1H-1,2,3-triazol-4-yl)ethyl)propane-1,3-diol;
(2) 2-amino-2-(2-(1-octyl-1H-1,2,3-triazol-4-yl)ethyl)propane-1,3-diol;
(3) 2-amino-2-(2-(1-(4-hexylphenethyl)-1H-1,2,3-triazol-4-yl)ethyl)propane-1,3-diol;
(4) 2-amino-2-(1-dodecyl-1H-1,2,3-triazol-4-yl)propane-1,3-diol;
(5) (E)-2-amino-2-(1-decyl-1H-1,2,3-triazol-4-yl)vinyl-1,3-diol;
(6) 2-amino-2-(2-(1-(8-phenyloctyl)-1H-1,2,3-triazolbutyl-4-yl)ethyl)propane-1,3-diol;
(7) N-(2-(1-dodecyl-1H-1,2,3-triazol-4-yl)-1,3-dihydroxypropan-2-yl)acetamide;
(8) N-(4-(1-decyl-1H-1,2,3-triazol-4-yl)-1-hydroxy-2-(hydroxymethyl)butan-2-yl)acetamide; and
(9) N-(4-(1-(4-hexylphenethyl)-1H-1,2,3-triazol-4-yl)-1-hydroxy-2-(hydroxymethyl)butan-2-yl)acetamide The compound represented by Chemical Formula 1 can be a compound represented by the following Chemical Formula 2.

[Chemical Formula 2]

In the present invention, the inflammatory bowel disease can be ulcerative colitis or Crohn's disease.

The pharmaceutical composition according to the present invention can be a preparation for oral administration and can be a preparation for parenteral administration.

The pharmaceutical composition according to the present invention can further include one or more other therapeutic agents suitable for the treatment of inflammatory bowel disease.

The pharmaceutical composition according to the invention can act as a functional antagonist for S1PR1 and S1PR4.

The pharmaceutical composition according to the present invention can be expected to have an effect of not causing cardiovascular side effects.

Advantageous Effects

The pharmaceutical composition according to the present invention acts as a functional antagonist for S1PR1 and S1PR4, and thus has an effect of preventing or treating inflammatory bowel disease.

In particular, the pharmaceutical composition according to the present invention acts as a functional antagonist for S1PR1 and S1PR4 among subtypes (S1P1, S1P2, S1P3, S1P4 and S1P5) of S1P receptors, and thus has an effect of preventing or treating inflammatory bowel disease and simultaneously has an effect of not causing cardiovascular side effects.

MODE FOR INVENTION

The descriptions disclosed in the present specification or application are exemplified solely for the purpose of describing embodiments according to the technical spirit of the present invention, embodiments according to the technical spirit of the present invention can be practiced in various forms other than the embodiments disclosed in the present specification or application, and the technical spirit of the present invention is not construed as being limited to the embodiments described in the present specification or application.

As used herein, "prevention" refers to all actions that suppress or delay the onset of a target disease by administering a pharmaceutical composition to an individual.

As used herein, "treatment" refers to all actions that alleviate or beneficially change symptoms of a target disease by administering a pharmaceutical composition to an individual.

Hereinafter, the present invention will be described in detail.

The pharmaceutical composition for preventing or treating inflammatory bowel disease according to the present invention includes, as an active ingredient, a material selected from a compound represented by the following Chemical Formula 1, an optical isomer thereof or a pharmaceutically acceptable salt thereof.

[Chemical Formula 1]

Here,
$R^1$ is hydrogen;
$R^2$ is hydrogen or an acetyl group;
X is a single bond, a $C_2$ alkylene, or a $C_2$ alkenylene;
A is a 5-membered heteroarylene including three N atoms;
B is a $C_{2-11}$ straight or branched alkylene;
C is a single bond or phenylene; and
D is selected from the group consisting of hydrogen, phenyl and a $C_{1-6}$ alkyl.
$R^2$ can be hydrogen.
X can be a $C_2$ alkylene.
B can be a straight $C_{2-11}$ alkylene.

Further, the present invention provides a method for preventing or treating inflammatory bowel disease, the method including: administering a material selected from the compound represented by Chemical Formula 1, an optical isomer thereof or a pharmaceutically acceptable salt thereof to an individual. The individual can be a human or an animal other than the human.

Since the material acts as a functional antagonist for S1PR1 and S1PR4, it is possible to provide a method for preventing or treating inflammatory bowel disease without causing cardiovascular side effects.

In addition, the present invention provides a use of a composition including, as an active ingredient, a material selected from the compound represented by Chemical Formula 1, an optical isomer thereof or a pharmaceutically acceptable salt thereof for preventing or treating inflammatory bowel disease.

Since the composition acts as a functional antagonist for S1PR1 and S1PR4, it is possible to provide a use of preventing or treating inflammatory bowel disease without causing cardiovascular side effects.

Furthermore, the compound represented by Chemical Formula 1 can be any one compound selected from the following compound group.

(1) 2-amino-2-(2-(1-decyl-1H-1,2,3-triazol-4-yl)ethyl)propane-1,3-diol;
(2) 2-amino-2-(2-(1-octyl-1H-1,2,3-triazol-4-yl)ethyl)propane-1,3-diol;
(3) 2-amino-2-(2-(1-(4-hexylphenethyl)-1H-1,2,3-triazol-4-yl)ethyl)propane-1,3-diol;
(4) 2-amino-2-(1-dodecyl-1H-1,2,3-triazol-4-yl)propane-1,3-diol;
(5) (E)-2-amino-2-(1-decyl-1H-1,2,3-triazol-4-yl)vinyl-1,3-diol;
(6) 2-amino-2-(2-(1-(8-phenyloctyl)-1H-1,2,3-triazolbutyl-4-yl)ethyl)propane-1,3-diol;
(7) N-(2-(1-dodecyl-1H-1,2,3-triazol-4-yl)-1,3-dihydroxypropan-2-yl)acetamide;
(8) N-(4-(1-decyl-1H-1,2,3-triazol-4-yl)-1-hydroxy-2-(hydroxymethyl)butan-2-yl)acetamide; and
(9) N-(4-(1-(4-hexylphenethyl) 1H-1,2,3-triazol-4-yl)-1-hydroxy-2-(hydroxymethyl)butan-2-yl)acetamide Furthermore, the compound represented by Chemical Formula 1 can be a compound represented by the following Chemical Formula 2 (hereinafter, referred to as 'NXC736'), 2-amino-2-(2-(1-decyl-1H-1,2,3-triazol-4-yl)ethyl)propane-1,3-diol.

[Chemical Formula 2]

The compound represented by Chemical Formula 1 can be used in the form of a pharmaceutically acceptable salt. As the salt, an acid addition salt formed by a pharmaceutically acceptable free acid can be used.

More specifically, the acid addition salt can be obtained from an inorganic acid such as hydrochloric acid, nitric acid, phosphoric acid, sulfuric acid, hydrobromic acid, hydriodic acid, nitrous acid, and phosphorous acid, a non-toxic organic acid such as aliphatic mono and dicarboxylates, phenyl-substituted alkanoates, hydroxy alkanoates and alkanedionates, aromatic acids, and aliphatic and aromatic sulfonic acid, and an organic acid such as acetic acid, benzoic acid, citric acid, lactic acid, maleic acid, gluconic acid, methanesulfonic acid, 4-toluenesulfonic acid, tartaric acid, and fumaric acid.

Further, the pharmaceutically non-toxic salts can include sulfates, pyrosulfates, bisulfates, sulfites, bisulfites, nitrates, phosphates, monohydrogen phosphates, dihydrogen phosphates, metaphosphates, pyrophosphates, chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butene-1,4-dioates, hexane-1,6-dioates, benzoates, chlorobenzoates, methyl benzoates, dinitrobenzoates, hydroxybenzoates, methoxybenzoates, phthalates, terephthalates, benzenesulfonates, toluenesulfonates, chlorobenzenesulfonates, xylenesulfonates, phenyl acetates, phenyl propionates, phenyl butyrates, citrates, lactates, β-hydroxybutyrates, glycolates, malates, tartrates, methanesulfonates, propanesulfonates, naphthalene-1-sulfonates, naphthalene-2-sulfonates, mandelates, and the like.

The acid addition salt can be prepared by a typical method. For example, the acid addition salt can be prepared by dissolving a derivative of the compound represented by Chemical Formula 1 in an organic solvent such as methanol, ethanol, acetone, methylene chloride, and acetonitrile and adding an organic acid or an inorganic acid thereto to filter and dry the resulting precipitate, or can be prepared by distilling a solvent and an excessive amount of acid under reduced pressure, and then drying the solvent and the acid to crystallize the resulting product under an organic solvent.

In addition, a pharmaceutically acceptable metal salt can be prepared by using a base. The pharmaceutically acceptable salt can be obtained by, for example, dissolving the compound represented by Chemical Formula 1 in an excessive amount of alkali metal hydroxide or alkaline earth metal hydroxide solution, filtering the non-soluble compound salt, evaporating the filtrate, and drying the resulting product. It is desirable to prepare a sodium, potassium or calcium salt as the metal salt. Furthermore, a silver salt corresponding thereto can be obtained by reacting an alkali metal or alkaline earth metal salt with a suitable silver salt (for example, silver nitrate).

Further, the pharmaceutical composition according to the present invention can not only contain the compound represented by Chemical Formula 1 and a pharmaceutically acceptable salt thereof as an active ingredient, but also can include, as an active ingredient, a material selected from a solvate, an optical isomer, a hydrate, and the like which can be prepared therefrom.

A pharmaceutical composition for preventing or treating inflammatory bowel disease, including the compound represented by Chemical Formula 1, an optical isomer thereof or a pharmaceutically acceptable salt thereof as an active ingredient can be changed to a preparation for oral administration and other types of preparations within a range exhibiting pharmacological activity.

The preparation for oral administration can be in the form of troches, lozenges, tablets, aqueous suspensions, oily suspensions, prepared powders, granules, emulsions, hard capsules, soft capsules, syrups, elixirs, or the like, but is not limited thereto.

In addition, to formulate the pharmaceutical composition according to the present invention into a preparation for oral administration, a binder such as lactose, saccharose, sorbitol, mannitol, starch, amylopectin, cellulose, or gelatin; an excipient such as dicalcium phosphate; a disintegrating agent such as corn starch or sweet potato starch; a lubricant such as magnesium stearate, calcium stearate, sodium stearyl fumarate, or polyethylene glycol wax; or the like can be used, and a sweetener; a fragrance; a syrup; or the like can be used. Furthermore, in the case of capsules, in addition to the above-mentioned materials, liquid carriers such as fatty oils can be further used.

A pharmaceutical composition for preventing or treating inflammatory bowel disease, including the compound represented by Chemical Formula 1, an optical isomer thereof or a pharmaceutically acceptable salt thereof as an active ingredient can be used by being formulated into various dosage forms suitable for parenteral administration.

Examples of a preparation for parenteral administration include injections, suppositories, powders for respiratory inhalation, aerosols for sprays, ointments, powders for application, oils, creams and the like, and are not limited thereto.

Further, to formulate the pharmaceutical composition according to the present invention into a preparation for parenteral administration, a sterilized aqueous solution, a non-aqueous solvent, a suspension agent, an emulsion, a lyophilized preparation, an external preparation and the like can be used. Specifically, as the non-aqueous solvent and the suspension agent, it is possible to use propylene glycol, polyethylene glycol, a vegetable oil such as olive oil, an injectable ester such as ethyl oleate, and the like.

When the pharmaceutical composition according to the present invention is formulated as an injection, the pharmaceutical composition can be mixed in water with a stabilizer or a buffer to be prepared into a solution or a suspension, which is then formulated for unit administration such as an ampoule or a vial. In addition, when the pharmaceutical composition according to the present invention is formulated as an aerosol, a propellant or the like can be blended with an additive so as to disperse a water-dispersed concentrate or wet powder. Furthermore, when the pharmaceutical composition according to the present invention is formulated as an ointment, a cream, or the like, the pharmaceutical composition can be formulated using, as a carrier, an animal oil, a vegetable oil, wax, paraffin, starch, tragacanth, cellulose derivatives, polyethylene glycol, silicone, bentonite, silica, talc, zinc oxide, or the like.

The pharmaceutical composition according to the present invention can further include one or more other therapeutic agents suitable for the treatment of inflammatory bowel disease.

The one or more other therapeutic agents suitable for the treatment of inflammatory bowel disease can be selected from the group consisting of corticosteroid drugs, non-steroidal anti-inflammatory drugs (NSAIDs), immunosuppressants, cytotoxic drugs and vasodilators. More specifically, examples of the one or more other therapeutic agents include ACE inhibitors, ARB or statin, corticosteroid or calcinerun inhibitors (for example: tacrolimus) and the like, but are not limited thereto. Further, the one or more other therapeutic agents suitable for the treatment of inflammatory bowel disease can be administered together or separately. When administered separately, the one or more therapeutic agents can be administered simultaneously or sequentially in any order. The dose and timing of the compound of Chemical Formula 1 or a pharmaceutically acceptable salt thereof and other therapeutic agents can be selected to achieve the desired combination therapeutic effect.

The pharmaceutical composition according to the present invention can further include a pharmaceutically acceptable carrier. "Pharmaceutically acceptable" means being typically used in the pharmaceutical field, which does not irritate an organism upon administration of the compound and does not inhibit the biological activity and properties of the administered compound.

The type of carrier is not particularly limited, and any carrier typically used in the art can be used. Non-limiting examples of the carrier include saline, sterile water, Ringer's solution, buffered saline, an albumin injection solution, lactose, dextrose, sucrose, sorbitol, mannitol, xylitol, erythritol, maltitol, maltodextrin, glycerol, ethanol, and the like. These can be used either alone or in a mixture of two or more thereof.

In addition, the pharmaceutical composition according to the present invention can be used by adding other pharmaceutically acceptable additives such as an excipient, a diluent, an antioxidant, a buffer or a bacteriostat to the pharmaceutical composition according to the present invention, if necessary. Furthermore, the pharmaceutical composition according to the present invention can be used by additionally adding a filler, an extender, a humectant, a disintegrating agent, a dispersing agent, a surfactant, a binder, a lubricant, or the like to the pharmaceutical composition according to the present invention, if necessary.

The pharmacologically effective amount and dose of the pharmaceutical composition according to the present invention to the human body may vary depending on the formulation method, administration method, administration time and/or administration route of the pharmaceutical composition. The above dosage may vary depending on various factors including the type and degree of the reaction to be achieved via administration of the pharmaceutical composition, the type, age, body weight, and general health status of an individual to which the composition is administered, the symptoms or severity of diseases, sex, diet, excretion, drugs used simultaneously or at different times in the corresponding individual, ingredients of other compositions, and the like and similar factors well known in the medical field, and the effective dose for desired treatment can be easily determined and prescribed by those of ordinary skill in the art. For example, the dose of the pharmaceutical composition according to the present invention to the human body can be 0.1 mg/kg to 1,000 mg/kg daily, preferably 10 mg/kg to 500 mg/kg. Further, the pharmaceutical composition according to the present invention can be administered once a day and can be administered in several divided doses. In addition, the administration route and administration method of the pharmaceutical composition according to the present invention may each be independent, and the method is not particularly limited. The pharmaceutical composition according to the present invention can be administered to follow any administration route and administration method as long as the active ingredient can reach the corresponding site.

The pharmaceutical composition according to the present invention can be administered by an oral administration or parenteral administration method. For example, as a method of parenteral administration, intravenous administration, intraperitoneal administration, intramuscular administration, transdermal administration, subcutaneous administration or the like can be used. In addition, a method of applying, spraying or inhaling the pharmaceutical composition according to the present invention to a diseased site can be used, but is not limited thereto. Furthermore, the pharmaceutical composition according to the present invention can be used for the treatment of inflammatory bowel disease in a subject in need thereof. In this case, the type of subject is not particularly limited, but can be a mammal, and preferably a human.

The S1PR1 receptor is predominantly present in lymphocytes, and is primarily responsible for regulating the release of lymphocytes from immune cells. The S1PR4 receptor is also present in lymphocytes to not only act on immune cell trafficking, but also act on T cell regulation, thereby being involved in the inflammatory response. Therefore, the compound of the present invention acts as a functional antagonist for the S1PR1 receptor to not only inhibit the release of lymphocytes, but also act on S1PR4 and show an effective anti-inflammatory effect, so there is an effect of preventing or treating inflammatory bowel disease. the present invention

Specifically, the compound of the present invention acts as a functional antagonist for these receptors by a mechanism of specifically binding to S1PR1 and S1PR4 and then causing them to flow into the cell and disappear, so there is an effect of preventing or treating inflammatory bowel disease. Further, the pharmaceutical composition according to the present invention may not cause cardiovascular side effects by acting as a functional antagonist for S1PR1 and S1PR4.

Hereinafter, the present invention will be described in more detail through Examples. These Examples are only for exemplifying the present invention, and it will be apparent to those of ordinary skill in the art that the scope of the present invention is not interpreted to be limited by these Examples.

EXAMPLES—PREPARATION OF COMPOUND REPRESENTED BY CHEMICAL FORMULA 1

The compound represented by Chemical Formula 1 of the present invention can be prepared by a method as described in Korean Patent Application Laid-Open No. 10-2017-0087813, and the method is the same as that of the examples described below. However, the method for preparing the compound represented by Chemical Formula 1 of the present invention is not limited thereto, and the compound can be prepared by a modified method within a range that can be modified by those skilled in the art.

Example 1–Preparation of 2-amino-2-(2-(1-decyl-1H-1,2,3-triazol-4-yl)ethyl)propane-1,3-diol

Step 1: Preparation of tert-butyl(2,2-dimethyl-5-((triisopropylsilyl)buta-1,3-diyn-1-yl)-1,3-dioxan-5-yl)carbamate After tert-butyl 5-ethynyl-2,2-dimethyl-1,3-dioxan-5-yl carbamate (1.25 g, 4.89 mmol) dissolved in methanol (30 mL) was added to a solution of CuCl (10 mg, 0.10 mmol), NH2OH·HCl (1.02 g, 14.67 mmol), and n-BuNH$_2$ (3.87 mL, 39.15 mmol) dissolved in methanol (50 mL) under N$_2$ gas conditions, 2-bromo-1-triisopropylsilyl acetylene (2.56 g, 9.78 mmol) dissolved in methanol (20 mL) was added dropwise thereto, the reaction mixture was well stirred at room temperature for 2 hours, and then the reaction was quenched with water and the resulting product was concentrated. After the concentrate was diluted with ethyl acetate and washed with brine, the organic layer was dried over MgSO$_4$, filtered in a vacuum state, and then concentrated. The resulting product was purified by flash column chromatography (hexane/EtOAc, 7:1) to prepare a target compound (1.85 g, 4.25 mmol, 87%) as a white solid.

Step 2: Preparation of tert-butyl(5-((1-decyl-1H-1,2,3-triazol-4-yl)ethynyl)-2,2-dimethyl-1,3-dioxan-5-yl)carbamate

1-Azidodecane (339 mg, 1.86 mmol), CuI (114 mg, 0.60 mmol), N,N-diisopropylethylamine (DIPEA) (0.63 mL, 3.6 mmol) and AgF (182 mg, 1.44 mmol) were added to an anhydrous DMF (12 mL) solution in which the compound (334 mg, 1.20 mmol) prepared in Step 1 was dissolved. After the reaction mixture was well stirred at room temperature for 12 hours, the reaction was quenched with saturated NH$_4$Cl, and then the resulting product was extracted twice with ethyl acetate, and the organic layer extract was washed with saturated NH$_4$Cl and brine. The product was dried over MgSO$_4$, and then concentrated under reduced pressure. The concentrate was purified by flash column chromatography (hexane/EtOAc, 6:1) to prepare a target compound (439 mg, 0.95 mmol, 79%) as a white solid.

Step 3: tert-butyl(5-(2-(1-decyl-1H-1,2,3-triazol-4-yl)ethyl)-2,2-dimethyl-1,3-dioxan-5-yl)carbamate 10% Pd/C (45 mg, 30 wt % of the compound prepared in Step 2) was added to a solution of the compound (149 mg, 0.32 mmol) prepared in Step 2 dissolved in methanol (30 mL). The flask was evacuated, and then filled with H$_2$ gas, the mixture was stirred at room temperature for 1 hour, filtered by Celite and concentrated, and then the precipitate was purified by flash column chromatography (hexane/EtOAc, 7:1 or 2:1) to prepare a target compound (110 mg, 0.24 mmol, 74%) as a colorless oil.

Step 4: Preparation of 2-amino-2-(2-(1-decyl-1H-1,2,3-triazol-4-yl)ethyl)propane-1,3-diol TFA (1.40 mL) was added to a CH$_2$Cl$_2$ (1.40 mL) solution in which the compound (65 mg, 0.14 mmol) prepared in Step 3 was dissolved at room temperature. The reactant was stirred for 12 hours, the solvent and the reagent were removed under reduced pressure, and then the concentrate was purified by flash column chromatography (CH$_2$Cl$_2$/MeOH/NH$_4$OH, 100:10:1) to prepare a target compound (36 mg, 0.11 mmol, 78%) as a while solid.

$^1$H NMR (400 MHz, CDCl$_3$) δ 0.86 (t, J=6.8 Hz, 3H), 1.23-1.29 (m, 14H), 1.85 (t, J=6.8 Hz, 2H), 1.92 (t, J=7.7 Hz, 2H), 2.47 (br s, 4H), 2.78 (t, J=7.8 Hz, 2H), 3.57 (dd, J=11.2, 26.9 Hz, 4H), 4.27 (t, J=7.3 Hz, 2H), 7.31 (s, 1H); $^{13}$C NMR (75 MHz, CDCl$_3$) δ 14.03, 19.21, 22.57, 26.50 (2C), 28.95 (2C), 29.03 (2C), 30.19, 31.70, 50.42, 60.05, 63.09 (2C), 121.34, 146.82; IR (CHCl$_3$) vmax; HRMS (FAB) calcd for C$_{17}$H$_{35}$N$_4$O$_2$ ([M+H]$^+$) 327.2760, found 327.2762.

Example 2—Preparation of 2-amino-2-(2-(1-octyl-1H-1,2,3-triazol-4-yl)ethyl)propane-1,3-diol The target compound was prepared in the same manner as in the reaction process of Example 1, except that 1-azidoctane was used instead of 1-azidodecane.

$^1$H NMR (400 MHz, CDCl$_3$) δ 0.86 (t, J=6.8 Hz, 3H), 1.24-1.29 (m, 10H), 1.84-1.91 (m, 4H), 2.48 (br s, 4H), 2.77 (t, J=7.4 Hz, 2H), 3.54 (q, J=12.2 Hz, 4H), 4.28 (t, J=7.2 Hz, 2H), 7.28 (s, 1H).

Example 3—Preparation of 2-amino-2-(2-(1-(4-hexylphenethyl)-1H-1,2,3-triazol-4-yl)ethyl)propane-1,3-diol The target compound was prepared in the same manner as in the reaction process of Example 1, except that 1-(2-azidoethyl)-4-hexylbenzene was used instead of 1-azidododecane.

Example 4—Preparation of 2-amino-2-(1-dodecyl-1H-1,2,3-triazol-4-yl)propane-1,3-diol The target compound was prepared in the same manner as in Example 1, except that bromotriisopropylsilane was used instead of 2-bromo-1-triisopropylsilyl acetylene used in Step 1 of Example 1, and 1-azidododecane was used instead of 1-azidodecane in Step 2.

$^1$H NMR (300 MHz, MeOD) δ 0.89 (t, J=6.7 Hz, 3H), 1.28-1.32 (m, 18H), 1.90-1.92 (m, 2H), 3.89-3.98 (m, 4H), 4.41 (t, J=7.1 Hz, 2H), 8.07 (s, 1H).

Example 5—Preparation of (E)-2-amino-2-(1-decyl-1H-1,2,3-triazol-4-yl)vinyl-1,3-diol

After the temperature of a THF (5 mL) solution, in which the compound prepared in Step 2 of Example 1 was dissolved, was lowered to −78° C., a THF solution (0.3 mmol), in which lithium aluminum hydride (LAH) was dissolved, was slowly added thereto. After the mixture was stirred 0° C. for 3 hours, the reaction was quenched with water, and the resulting product was extracted twice with CH$_2$Cl$_2$. The organic layer was washed with brine, dried over MgSO$_4$, and then concentrated under vacuum. The concentrate was purified by flash column chromatograph (CH$_2$Cl$_2$/MeOH, 20:1) to prepare a target compound as a white solid. Thereafter, the target compound was prepared in the same manner as in the reaction process of Step 4 of Example 1. (24 mg, 0.074 mmol, 74%)

Example 6—Preparation of 2-amino-2-(2-(1-(8-phenyloctyl)-1H-1,2,3-triazolbutyl-4-yl)ethyl)propane-1,3-diol The target compound was prepared in the same manner as in Example 1, except that 8-azidooctylbenzene was used instead of 1-azidododecane used in Step 2 of Example 1.

Example 7—Preparation of N-(2-(1-dodecyl-1H-1,2,3-triazol-4-yl)-1,3-dihydrooxypropan-2-yl)acetamide Acetic anhydride (0.2 mL), MeOH (1 mL), and an aqueous saturated NaHCO$_3$ solution (1 mL) were added to the compound (50 mg, 1 eq, 0.15 mmol) prepared in Example 4, the resulting mixture was stirred for 30 minutes, and then concentrated, the reaction was quenched with an aqueous ammonium chloride solution, and then the resulting product was extracted twice with CH$_2$Cl$_2$, dried over MgSO$_4$, and concentrated to prepare the target compound at a yield of 98% without a separate purification process (54 mg, 98%).

$^1$H NMR (300 MHz, MeOD) δ 0.89 (t, J=6.7 Hz, 3H), 1.28-1.32 (m, 18H), 1.86-1.96 (m, 2H), 2.00 (s, 3H), 4.02 (q, J=11.2 Hz, 4H), 4.35 (t, J=7.2 Hz, 2H), 7.84 (s, 1H).

Example 8—Preparation of N-(4-(1-decyl-1H-1,2,3-triazol-4-yl)-1-hydroxy-2-(hydroxymethyl)butan-2-yl)acetamide The target compound was prepared in a manner similar to the acetylation reaction performed in Example 7 using the compound prepared in Example 1 as a starting material.

$^1$H NMR (300 MHz, MeOD) δ 0.86 (t, J=6.8 Hz, 3H), 1.23-1.32 (m, 14H), 1.86-1.92 (m, 2H), 1.94 (s, 3H), 1.99-2.02 (m, 2H), 2.47 (m, 2H), 3.62 (dd, J=11.2, 26.9 Hz, 4H), 4.31 (t, J=7.3 Hz, 2H), 7.31 (s, 1H).

Example 9—Preparation of N-(4-(1-(4-hexylphen-ethyl)-1H-1,2,3-triazol-4-yl)-1-hydroxy-2-(hy-droxymethyl)butan-2-yl)acetamide The target compound was prepared in a manner similar to the acetylation reaction performed in Example 7 using the compound prepared in Example 3 as a starting material.

Experimental Example 1: Confirmation of Suppressive Effect of NXC736 on Mouse Immune Cells FTY720 (fingolimod) is a therapeutic agent for multiple sclerosis, which has an action mechanism of suppressing lymphocytes from entering into the central nervous system by reversibly capturing a part of lymphocytes in lymph nodes or bone marrow to sequester lymphocytes in secondary lymphoid organs or reducing the number of activated lymphocytes that reach the brain by reducing the number of lymphocytes circulating in the bloodstream.

To confirm whether NXC736, which acts on the S1P receptor, also has an effect on lymphocyte reduction, the effect of NXC736 on immune cells was evaluated. After oral administration of NXC736 at 3 mg/kg/day to mice, changes in lymphocytes in the peripheral blood (PB) stream and bone marrow (BM) were classified for T cells, CD4T cells, and CD8T cells, and FACS analysis was performed at 0, 4, 8, 12, 24, and 36 hours after the administration of a test material. A cell number was measured and shown as a percentage (%) of a control based on 0 time.

Figure 1:
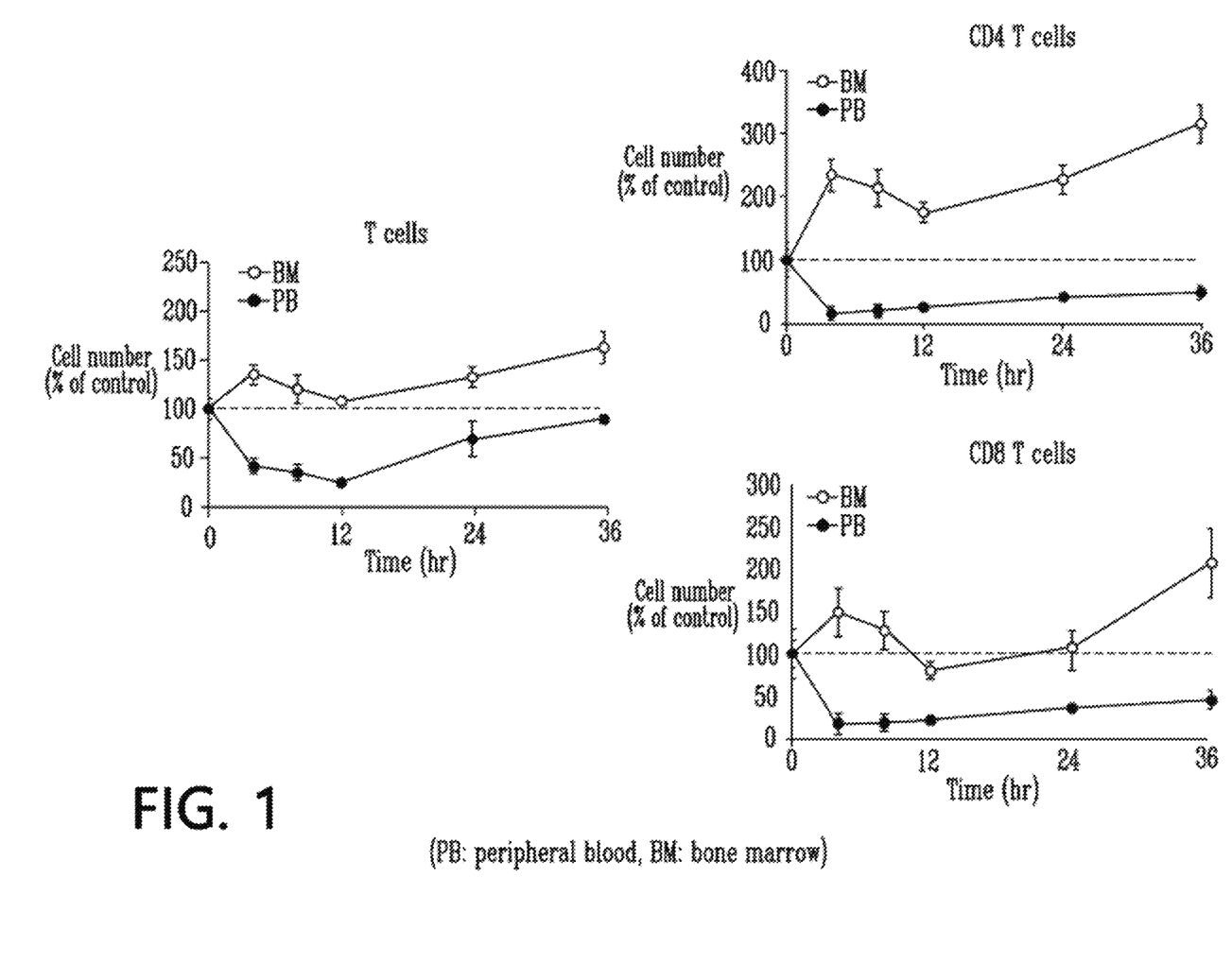
FIG. 1 is a set of graphs showing changes in cell number of the total T cells and T cell subtypes of mice after oral administration of NXC736 (3 mg/kg/day).

Referring to FIG. 1, it could be confirmed that in peripheral blood (PB) stream, all the cell numbers of T cells, CD4 T cells, and CD8 T cells were reduced to the levels of 40.6%/41.6%, 16.4%/17.6%, and 5.9%/9.3% from 0 hour to 4 hours by the administration of NXC736 at 3 mg/kg. The reduction was maintained until 12 hours, but the level recovered to 88.9% at 36 hours. Dose dependency appeared in T cells 24 hours after administration, and in the case of CD4 T cells and CD8 T cells, a dose-dependent reduction effect could be confirmed from 4 hours to 24 hours after the administration.

In bone marrow (BM), the cell number was 135% and 120% 4 hours after administration of NXC7363 at 3 mg/kg, and 131% and 118% 24 hours after the administration, so the distribution of T cells could be confirmed. This is determined to be a phenomenon in which the release of T cells is suppressed because NXC736 causes receptor internalization.

After the administration of NXC736 at 3 mg/kg, a phenomenon in which the cell number in T cells was reduced from 4 hours occurred, and it could be confirmed that the suppressive effect was maintained to some extent until 24 hours and then the cell number was recovered. In conclusion, it could be confirmed that the administration of NXC736 reduced the number of lymphocytes circulating in the bloodstream and exhibited an immunosuppressive effect.

Experimental Example 2: Confirmation of Suppressive Effect of NXC736 on Rat Immune Cells To evaluate the effect of NXC736 on rat immune cells, after oral administration of NXC736 at 10 mg/kg/day to SD rats, changes in lymphocytes in the peripheral blood (PB) stream and bone marrow (BM) were classified for T cells, CD4 T cells, and CD8 T cells, and FACS analysis was performed at 0, 4, 8, 12, 24, 36, and 48 hours after the administration of a test material. A cell number was measured and shown as a percentage (%) of a control based on 0 time, and the numbers of T cells, CD4 T cells, and CD8 T cells were measured and shown as a percentage (%) of a control based on 0 time.

Figure 2:
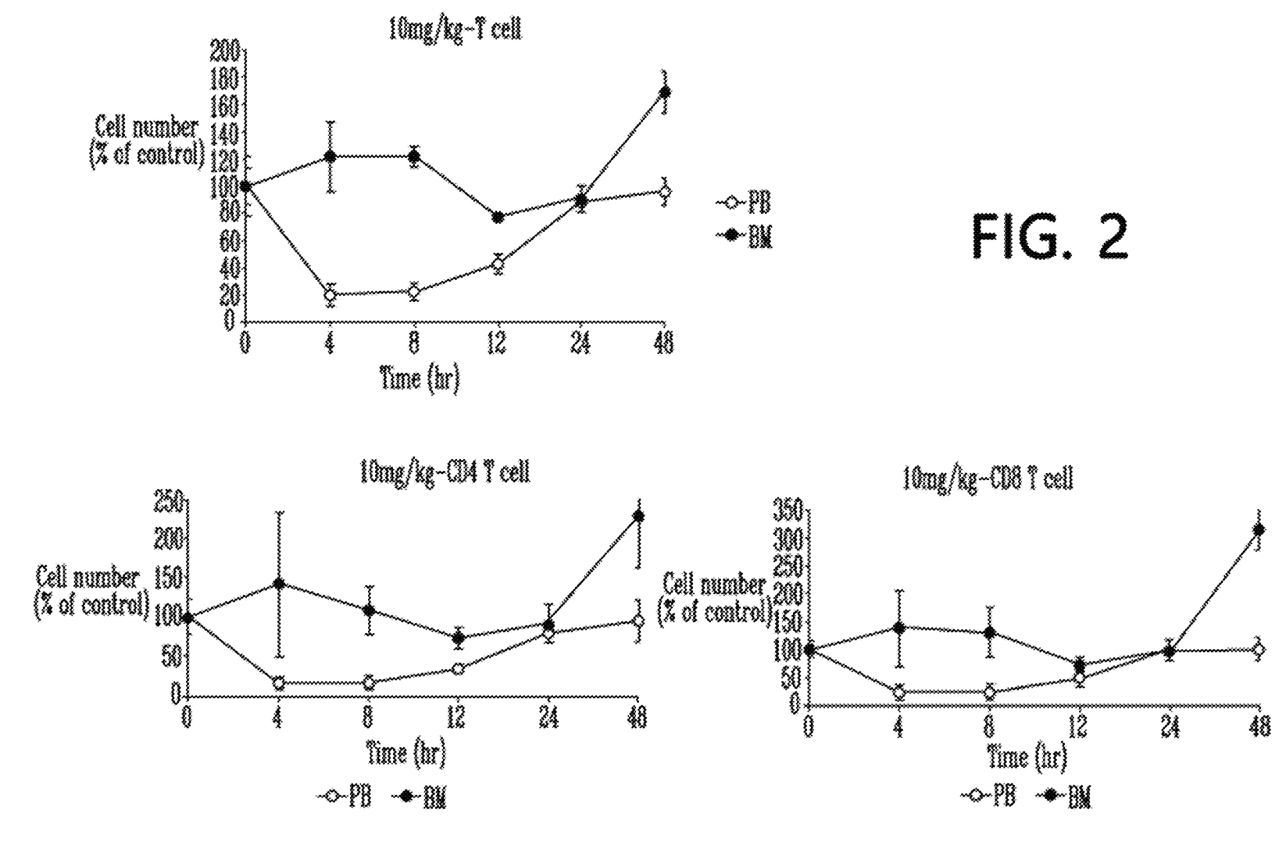
FIG. 2 is a set of graphs showing changes in cell number of the total T cells and T cell subtypes of rats after oral administration of NXC736 (10 mg/kg/day).

Referring to FIG. 2, it could be confirmed that the number of T cells was reduced from 4 hours in the peripheral blood (PB) stream after the administration of NXC736. The suppressive effect was shown in a dose-dependent manner (70%, 80%, and 87%), and it could be confirmed that the suppressive effect was maintained until 24 hours by administration of NXC736 at 10 mg/kg. On the contrary, in the bone marrow (BM), it could be confirmed that there was no change or a tendency to increase.

Through this study, it could be confirmed that NXC736 exhibits an immunosuppressive effect by reducing the number of lymphocytes in the peripheral blood (PB) stream after oral administration. Further, in the bone marrow (BM), it could be confirmed that there was no change or a tendency to increase. It is determined that such an effect is associated with a mechanism in which NXC736 acts as a functional antagonist on S1P receptors present in lymph nodes, bone marrow (BM), and the like to suppress the release of lymphocytes.

Experimental Example 3: Confirmation of Efficacy in Suppressing Inflammatory Bowel Disease Using Mouse DSS Induced Model The effect of NXC736 for inflammatory bowel disease was evaluated using a dextran sulfate sodium (DSS)-induced colitis model. In the mouse model, inflammatory bowel disease was induced by administering DSS to mice in drinking water at a concentration of 2.5%. Treatment groups consisted of a test group administered NXC736, a positive control administered ozanimod or methotrexate (MTX), a vehicle group and a normal control, and each group had n=10. In the model in which inflammatory bowel disease was induced, NXC736, which is the compound of the present invention, was orally administered at a dose of 5 and 10 mg/kg once a day for 7 days, ozanimod as a positive control material was orally administered at 5 mg/kg once a day, and methotrexate (MTX) as a positive control material was intraperitoneally administered at 3 mg/kg three times a week.

Figure 3:
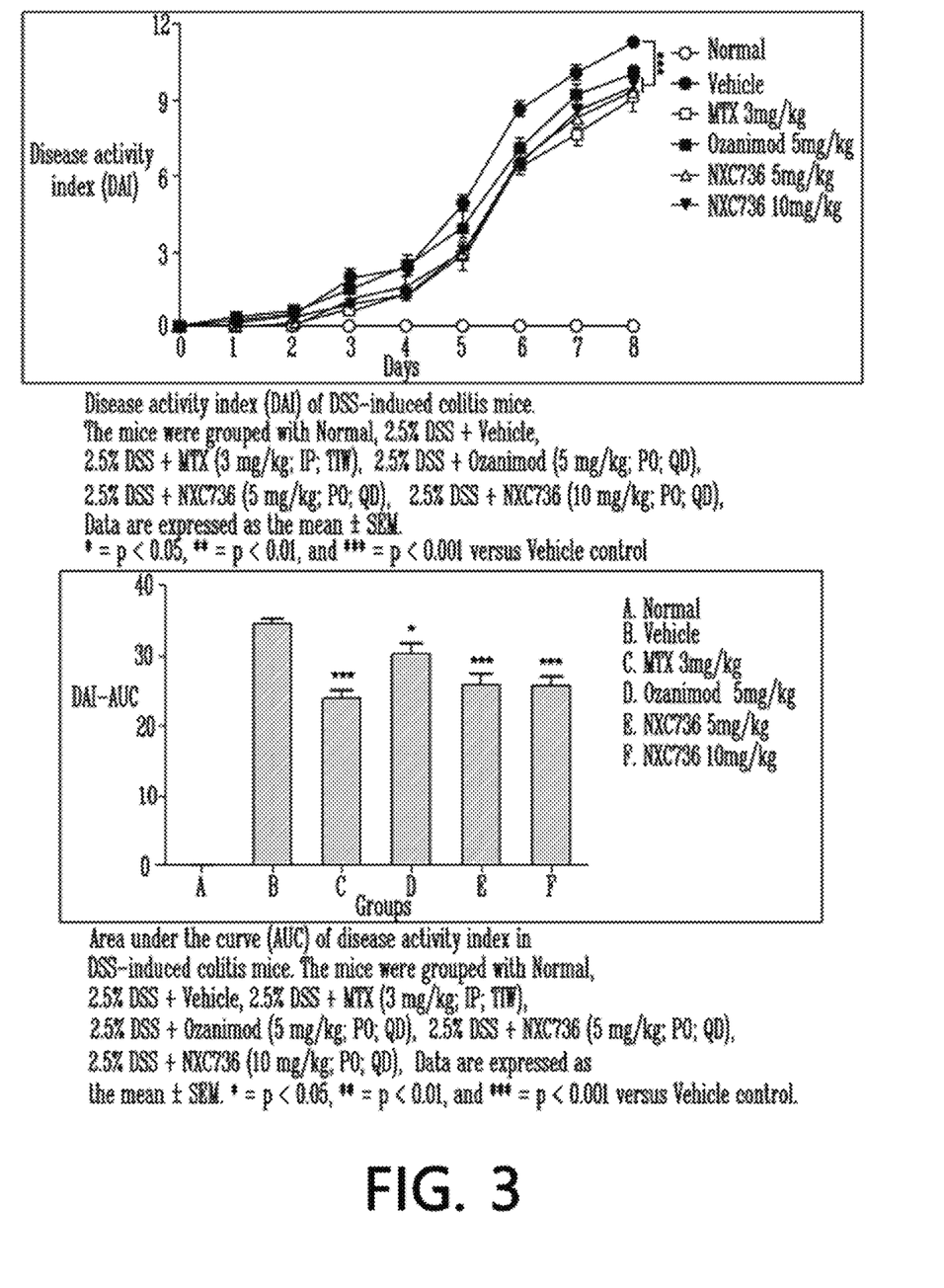
FIG. 3 is a set of graphs showing an effect of NXC736 (5 and 10 mg/kg/day) on the suppression of inflammatory bowel disease in a DSS-induced colitis mouse model.

FIG. 3 illustrates the disease activity index (DAI) of DSS-induced colitis mice and the area under the disease activity index curve (AUC) of DSS-induced colitis mice. The DAI shows the total score of body weight loss compared to the initial body weight of mice, stool concentration (stool consistency), and degree of intestinal bleeding. The calculation criteria for DAI are shown in the following Table 1, and the DAI was evaluated on days 0, 1, 2, 3, 4, 5, 6, 7, and 8.

TABLE 1

| Score | Amount of body weight loss compared to initial body weight | Stool concentration (Stool consistency) | Degree of intestinal bleeding (Intestinal bleeding) |
|---|---|---|---|
| 0 | <1% | Normal | No occult blood detected (Negative hemoccult) |
| 1 | 1 to 5% | Soft but still formed | Occult blood detected (Weak luminol intensity) |
| 2 | 6 to 10% | Soft | Occult blood detected (Strong luminol intensity) |
| 3 | 11 to 18% | Very soft; wet | With the naked eye Confirmation of blood in stool |
| 4 | >18% | Watery diarrhea | Intestinal bleeding |

Referring to FIG. 3, in all the administration groups of the positive control material MTX at 3 mg/kg, ozanimod at 5 mg/kg, NXC736 at 5 mg/kg, and NXC736 at 10 mg/kg, a statistically significant reduction effect could be confirmed compared to the negative control (vehicle).

In particular, as a result of administration of NXC736 at 5 mg/kg and NXC736 at 10 mg/kg, it could be confirmed that the clinical indicators according to the amount of body weight loss, the stool concentration, and the degree of intestinal bleeding showed equivalent values or more compared to those of ozanimod which is used as a targeted therapeutic agent for ulcerative colitis in the related art.

The above evaluation results were statistically analyzed between the negative control and the test group or between the two test groups, and a Student's test or Mann Whitney U test showed a significance level with a p value of 0.05 or less for comparison between the groups.

From this, it could be confirmed that NXC736 is a material having a suppressive effect on inflammatory bowel disease.

Experimental Example 4: Evaluation of Effect of NXC736 on Cardiovascular System

1) Evaluation of Effect of NXC736 on HEK293 Cells Overexpressing hERG Gene

The effect of NXC736 on human ether-a-go-go related gene (hERG) channel currents was evaluated by applying NXC736 to HEK-293 cells in which hERG potassium ion channels were stably expressed by introducing hERG. NXC736 was set at a concentration of 1, 3, 10 and 30 μM, the negative control was treated with an external bath solution, and 3 cells were applied for each concentration. The positive control was treated with E-4031 at a concentration of 0.1 μM. Furthermore, on the day of each experiment, any one cell for which the recording of hERG channel currents for the negative control material or the test material at each concentration was completed was treated.

Figure 4:
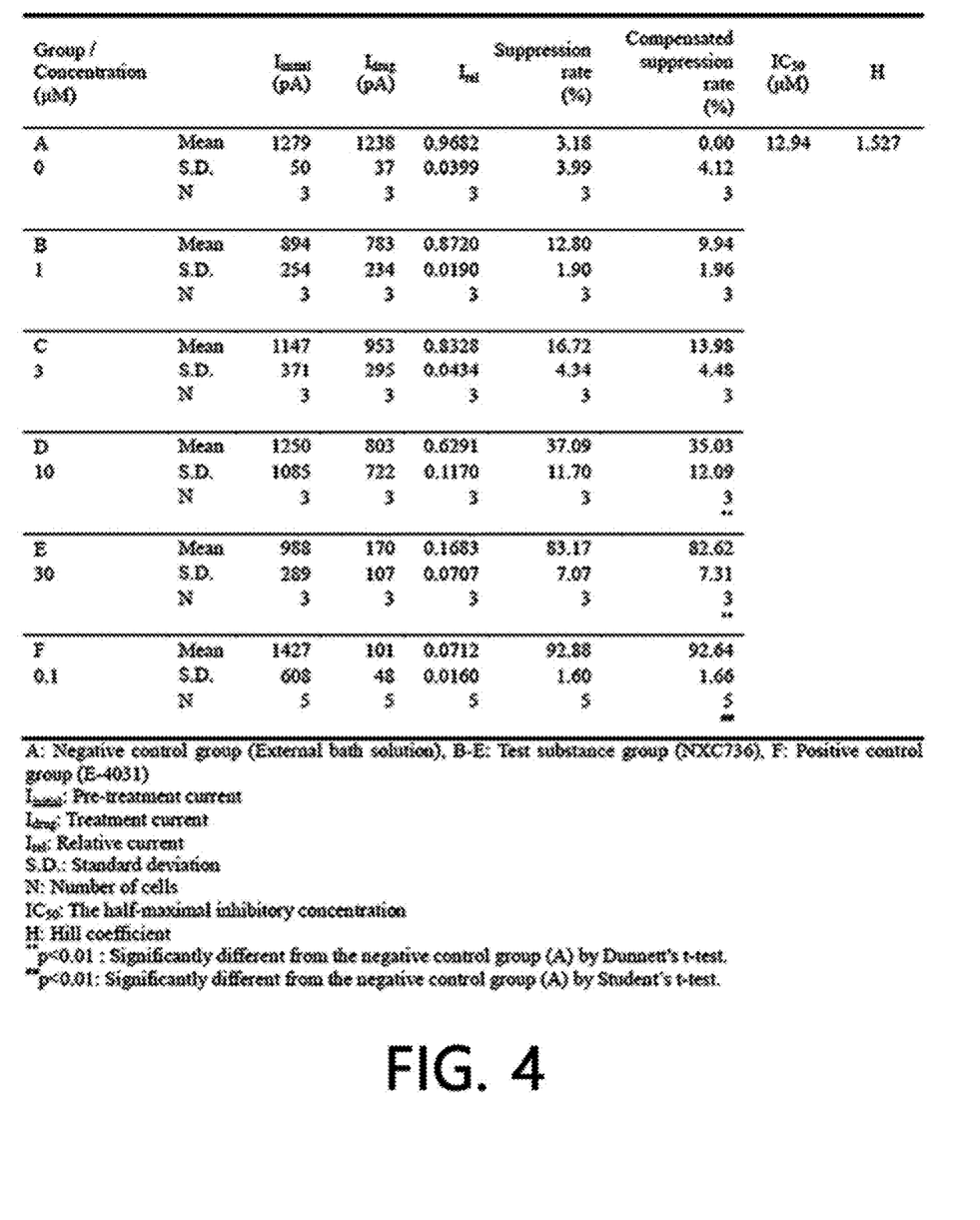
FIG. 4 is a table of evaluating and testing an effect of NXC736 (1, 3, 10, and 30 μM) in HEK293 cells in which a hERG gene is overexpressed.

Referring to FIG. 4, the compensated suppression rates (%) of hERG channel currents of NCX736 (B to E groups) at a concentration of 1, 3, 10 and 30 μM were 9.94±1.96, 13.98±4.48, 35.03±12.09 and 82.62±7.31% (n=3), respectively, and the compensated suppression rate (%) of hERG channel currents of the negative control (A group) exhibited a value of 0±4.12 (n=3). That is, it could be confirmed that NCX736 (D and E groups) at a concentration of 10 and 30 μM exhibited a statistically significant difference in value compared to the negative control (A group).

Under the same conditions, the cell was treated with E-4031 at a concentration of 0.1 μM used as the positive control (F group). The compensated suppression rate (%) of hERG channel currents exhibited a high value of 92.64±1.66% (n=5). Based on these results, it is determined that this test method is a method suitable for evaluating the effect of NCX736 on hERG channel currents.

In the evaluation of the effect on hERG channel currents using HEK-293 cells into which the hERG gene was introduced under the above conditions, as a result of treating the cells with a test material NXC736 at a concentration of up to 30 μM, the compensated suppression rate of hERG channel currents was 82.62±7.31%, and a $K^+$ ion channel inhibitory capacity (IC50) was calculated to be 12.94 μM (Hill coefficient: 1.527). Therefore, it could be confirmed that NXC736 is a material that does not inhibit hERG potassium channel activity and does not cause cardiac abnormalities.

2) Confirmation of Effect on Cardiovascular System Using Beagle Dogs

NXC736 was orally administered to four male beagle dogs under unanesthetized and unrestrained conditions with a remote transmitter inserted. Thereafter, the effect of NXC736 on the cardiovascular system was evaluated by measuring the heart rate for four beagle dogs, and it was confirmed with the naked eye whether abnormal symptoms appeared.

In this experiment, the experimental material was administered to each of the four beagle dogs over four steps. A 0.5% MC aqueous solution, which is an excipient, was administered as a control material in the first administration step (NXC7365 at 0 mg/kg), NXC736 at 12.5 mg/kg was administered in the second administration step, NXC736 at 25 mg/kg was administered in the third administration step, and NXC736 at 50 mg/kg was administered in the fourth administration step. The 1st to 4th administrations were performed at intervals of 1 week. In addition, at 0 hours before administration of the experimental material and at 0.5 hours, 1 hour, 2 hours, 3 hours, 4 hours, 6 hours, 8 hours, 12 hours and 24 hours after administration of the test material, the beagle dog's heart rate were measured.

Figure 5:
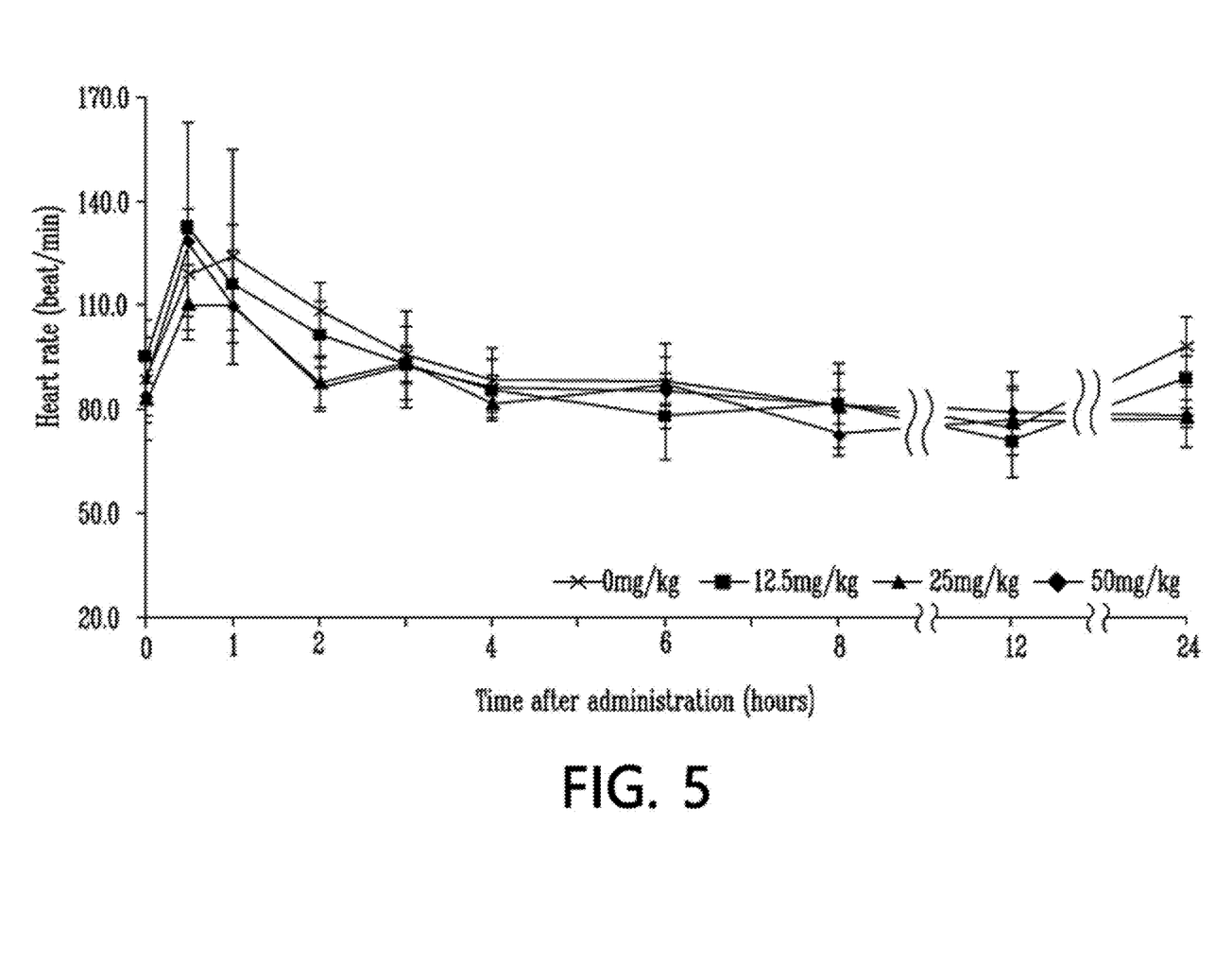
FIG. 5 is a graph showing the results of measuring a heart rate in beagle dogs after oral administration of NXC736 (12.5, 25, and 50 mg/kg).

Referring to FIG. 5, it could be confirmed that no change in heart rate appeared even though NXC736 was administered at a dose of 12.5, 25 and 50 mg/kg.

In addition, as a result of observing general symptoms of beagle dogs with the naked eye, no abnormal symptoms by administration of NXC736 at a dose of 12.5, 25 and 50 mg/kg were observed.

As described above, according to the results of evaluating inflammatory bowel disease suppression efficacy using a DSS-induced mouse model, the heart rate of beagle dogs administered NXC736, and the results of confirming whether abnormal symptoms appeared with the naked eye, it could be confirmed that the pharmaceutical composition including, as an active ingredient, the compound represented by Chemical Formula 1 according to the present invention, an optical isomer thereof or a pharmaceutically acceptable salt thereof acts as a functional antagonist for S1PR1 and S1PR4, and thus has an effect of preventing or treating inflammatory bowel disease. Furthermore, it could be confirmed that the pharmaceutical composition according to the present invention acts as a functional antagonist for S1PR1 and S1PR4 among subtypes (S1P1, S1P2, S1P3, S1P4 and S1P5) of S1P receptors, and thus has an effect of preventing or treating inflammatory bowel disease and simultaneously has an effect of not causing cardiovascular side effects.

The invention claimed is:

1. A method for preventing or treating inflammatory bowel disease, comprising administering a compound represented by the following Chemical Formula 1, an optical isomer thereof or a pharmaceutically acceptable salt thereof to a subject in need thereof:

[Chemical Formula 1]

wherein,
R$^1$ is hydrogen;
R$^2$ is hydrogen or an acetyl group;
X is a single bond, a C$_2$ alkylene, or a C$_2$ alkenylene;
A is a 5-membered heteroarylene including three N atoms;
B is a C$_{2-11}$ straight or branched alkylene;
C is a single bond or phenylene; and
D is selected from the group consisting of hydrogen, phenyl and a C$_{1-6}$ alkyl, wherein the compound represented by Chemical Formula 1 is any one compound selected from the following compound group:
(1) 2-amino-2-(2-(1-decyl-1H-1,2,3-triazol-4-yl)ethyl)propane-1,3-diol;
(2) 2-amino-2-(2-(1-octyl-1H-1,2,3-triazol-4-yl)ethyl)propane-1,3-diol;
(3) 2-amino-2-(2-(1-(4-hexylphenethyl)-1H-1,2,3-triazol-4-yl)ethyl)propane-1,3-diol;
(6) 2-amino-2-(2-(1-(8-phenyloctyl)-1H-1,2,3-triazol-butyl-4-yl)ethyl)propane-1,3-diol;
(8) N-(4-(1-decyl-1H-1,2,3-triazol-4-yl)-1-hydroxy-2-(hydroxymethyl)butan-2-yl)acetamide; and
(9) N-(4-(1-(4-hexylphenethyl)-1H-1,2,3-triazol-4-yl)-1-hydroxy-2-(hydroxymethyl)butan-2-yl)acetamide.

2. The method of claim 1, wherein the compound represented by Chemical Formula 1 is a compound represented by the following Chemical Formula 2:

[Chemical Formula 2]

3. The method of claim 1, wherein the inflammatory bowel disease is ulcerative colitis or Crohn's disease.

4. The method of claim 1, wherein the compound, the optical isomer thereof or the pharmaceutically acceptable salt thereof is administered orally or parenterally.

5. The method of claim 1, wherein the compound, the optical isomer thereof or the pharmaceutically acceptable salt thereof acts as a functional antagonist for S1PR1 and S1PR4.

6. The method of claim 5, wherein the compound, the optical isomer thereof or the pharmaceutically acceptable salt thereof does not cause cardiovascular side effects.

* * * * *